US009567266B2

(12) United States Patent
Ishibashi et al.

(10) Patent No.: US 9,567,266 B2
(45) Date of Patent: Feb. 14, 2017

(54) OLEFIN PRODUCTION METHOD

(71) Applicant: MITSUI CHEMICALS, INC., Tokyo (JP)

(72) Inventors: Masayasu Ishibashi, Takaishi (JP); Tsuneyuki Ohkubo, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 114 days.

(21) Appl. No.: 14/372,370

(22) PCT Filed: Dec. 20, 2012

(86) PCT No.: PCT/JP2012/083124
§ 371 (c)(1),
(2) Date: Jul. 15, 2014

(87) PCT Pub. No.: WO2013/108543
PCT Pub. Date: Jul. 25, 2013

(65) Prior Publication Data
US 2014/0371502 A1    Dec. 18, 2014

(30) Foreign Application Priority Data

Jan. 20, 2012   (JP) ................................ 2012-010148
Jan. 20, 2012   (JP) ................................ 2012-010149

(51) Int. Cl.
*C07C 1/24* (2006.01)
*C07C 1/207* (2006.01)

(52) U.S. Cl.
CPC ................. *C07C 1/24* (2013.01); *C07C 1/207* (2013.01); *C07C 2521/02* (2013.01); *C07C 2521/08* (2013.01); *C07C 2521/12* (2013.01); *C07C 2523/02* (2013.01); *C07C 2523/04* (2013.01)

(58) Field of Classification Search
CPC ........... B01J 37/02; B01J 37/03; B01J 37/036; B01J 13/0052; B01J 20/28047
USPC ................................ 585/638, 639, 640, 641
See application file for complete search history.

(56) References Cited

U.S. PATENT DOCUMENTS

| | | | |
|---|---|---|---|
| 2,377,026 | A | 5/1945 | Miller |
| 5,017,729 | A | 5/1991 | Fukuhara et al. |
| 6,225,253 | B1 | 5/2001 | Debras |
| 6,423,663 | B2 | 7/2002 | Debras |
| 6,482,901 | B1 | 11/2002 | Debras |
| 8,552,239 | B2 | 10/2013 | Ohkubo et al. |
| 8,680,355 | B2 | 3/2014 | Ohkubo et al. |
| 9,067,199 | B2 * | 6/2015 | Nesterenko ............ B01J 29/06 |
| 2004/0194295 | A1 | 10/2004 | Green |
| 2010/0168491 | A1 | 7/2010 | Haishi |

FOREIGN PATENT DOCUMENTS

| | | |
|---|---|---|
| CN | 102125867 A | 7/2011 |
| CN | 102219630 | 10/2011 |
| DE | 84 378 | 9/1971 |
| GB | 2377026 A1 | 12/2002 |
| JP | 26414 | 1/1990 |
| JP | 2-174737 | 7/1990 |
| JP | 3-41035 | 2/1991 |
| JP | 200053717 | 2/2000 |
| JP | 2010-241790 | 10/2010 |
| WO | 2010/064500 | 6/2010 |
| WO | 2010/106966 | 9/2010 |

OTHER PUBLICATIONS

Fahim RB. "Dehydration of Ethyl Alcohol on Alumina-Coated Silica." J. Appl. Chem. 1969. vol. 19 pp. 356-358.*
Chinese Office Action dated Mar. 26, 2015 issued in the corresponding Chinese patent application No. 201280067330.1.
International Search Report, Application No. PCT/2012/083124, dated Mar. 19, 2013.
Extended European Search Report dated Jul. 20, 2015 which was issued in connection with corresponding European patent application No. 12865945.5.
Taiwanese Office Action dated Apr. 1, 2016 issued in the corresponding Taiwanese patent application No. 102101454.
Chinese Office Action dated Apr. 29, 2016 issued in the corresponding Chinese patent application No. 201280067330.1.
Evidence 1: Basic Organic Chemistry (the Third Edition) Volume One, published by Higher Education Press and printed for the first time in Jun. 2005, pp. 275-277 with English translation.
Evidence 2: Foundations of Organic Chemistry, published by Ocean Press and printed for the first time in Jul. 2008, pp. 189-191 with English translation.
Evidence 3: Organic Chemistry, published by Huazhong University of Science and Technology Press and printed for the first time in Aug. 2007, pp. 234 and 235 with English translation.
Evidence 4: Organic Chemistry, published by China Agriculture Press and printed for the first time in Jul. 2007, pp. 103 and 104 with English translation.
Communication under Rule 71(3) EPC dated Jul. 7, 2016 issued in the corresponding European patent application No. 12865945.5.

* cited by examiner

Primary Examiner — Sharon Pregler
(74) Attorney, Agent, or Firm — Rankin, Hill & Clark LLP

(57) ABSTRACT

The invention has objects of providing an olefin production method which can produce an olefin with high efficiency by the dehydration reaction of an alcohol even in the presence of a ketone without the occurrence of side reactions such as the Aldol condensation of the ketone, as well as providing an olefin production method which can produce an olefin with high activity and high selectivity in a single reaction step by directly reacting a corresponding ketone and hydrogen. The former olefin production method of the invention produces an olefin from an alcohol using a silica gel (A) as a dehydration catalyst which is obtained by bringing a silica gel (X) prepared from an alkyl orthosilicate into contact with a water-soluble aluminum compound and calcining the contact product or is obtained from a wet-process silica gel (Y) prepared from an alkali silicate and which contains an aluminum compound at 10 to 1000 ppm in terms of aluminum element as well as an alkali metal and an alkaline earth metal at a total of 0 to 350 ppm. The latter olefin production method produces an olefin from a ketone and hydrogen in a single reaction step in the presence of the silica gel (A) and a silver-containing inorganic substance (B).

15 Claims, No Drawings

OLEFIN PRODUCTION METHOD

TECHNICAL FIELD

The present invention relates to an olefin production method, in particular to a method for producing olefins using a silica gel as a dehydration catalyst.

BACKGROUND ART

A reaction between benzene and propylene gives cumene. The oxidation of cumene results in cumene hydroperoxide. The cumene hydroperoxide is acid decomposed into phenol and acetone. A combination of these known reactions is the cumene process which is currently a mainstream method for the production of phenol.

The cumene process gives acetone as a by-product. This by-production is advantageous when both phenol and acetone are demanded. However, if the amount of by-product acetone is in excess of demand, the economic efficiency can be deteriorated due to the price difference between acetone and propylene which is a starting material. Methods have been then proposed in which the by-product acetone is converted into propylene through various reactions and is reused as a material in the cumene process.

Acetone is readily hydrogenated into isopropyl alcohol. A process has been then proposed in which isopropyl alcohol thus obtained is intramolecularly dehydrated into propylene and the propylene is reacted with benzene to give cumene. That is, acetone is reused as a material in the cumene process by being converted into propylene through reactions in two stages (Patent Literature 1).

Further, Patent Literatures 2 and 3 propose methods for producing propylene from acetone and hydrogen in one stage, namely, through a single reaction step. In order to implement the reuse of acetone on an industrial level through such a one-stage reaction, it is necessary not only that the process be a practical process capable of producing propylene from acetone with high activity and high selectivity but also that the catalyst used in the process be easily available or readily producible at low cost. For example, phosphotungstates described in Patent Literature 3 as examples of heteropoly acid salts are allegedly effective for catalyzing the dehydration reaction of isopropyl alcohol. However, the production of such phosphotungstates entails multiple reaction steps. Further, the establishment of a practical method capable of converting acetone into propylene as well as of producing olefins from corresponding general ketones with high selectivity is valuable in various fields of industry other than the phenol industry.

For example, Patent Literature 4 describes a method in which propylene is obtained in one stage through the hydrogenation of acetone at 400° C. in the presence of a Cu (25%)-ZnO (35%)-Al$_2$O$_3$ (40%) catalyst. However, the acetone conversion is as low as 89% in spite of the fact that the reaction temperature is high at 400° C. Further, the propylene selectivity obtained by this method is as low as 89% because of the side reaction hydrogenating the produced propylene into propane. According to the findings by the present inventors, it has been confirmed that the hydrogenation of acetone into propylene in the presence of a mixed catalyst including a hydrogenation catalyst and a general dehydration catalyst can be accompanied by the Aldol condensation of acetone by the dehydration catalyst with the result that the formed Aldol reaction product can further undergo a dehydration reaction, a decomposition reaction and a hydrogenation reaction. That is, by-products are likely to be derived from acetone that is a starting material. Further, the use of a general dehydration catalyst can induce other reactions such as the oligomerization of formed propylene. Thus, the present inventors consider that the design and selection of a catalyst, in particular a dehydration catalyst, are the technical key to successfully producing propylene from acetone and hydrogen.

CITATION LIST

Patent Literatures

Patent Literature 1: JP-A-H02-174737
Patent Literature 2: WO 2010/064500
Patent Literature 3: WO 2010/106966
Patent Literature 4: East German Patent DD84378

SUMMARY OF INVENTION

Technical Problem

It is a first object of the invention to provide a dehydration catalyst that allows a dehydration reaction of an alcohol to take place with high efficiency even in the presence of a ketone without the occurrence of side reactions such as the Aldol condensation of the ketone.

Further, it is a second object of the invention to provide a novel method which can produce an olefin with high activity and high selectivity in a single reaction step by directly reacting the corresponding ketone and hydrogen. In particular, an object of the invention is to provide a method which can produce propylene with high activity and high selectivity by directly reacting acetone and hydrogen.

Solution to Problem

The present inventors carried out studies in order to achieve the above objects. As a result, the present inventors have found that an olefin represented by General Formula (II) below can be produced from an alcohol of General Formula (I) below with high activity and high selectivity by using a chemically treated silica gel (A) as a dehydration catalyst which contains an aluminum compound at 10 to 1000 ppm in terms of aluminum element as well as an alkali metal and an alkaline earth metal at a total of 0 to 350 ppm. (This invention is sometimes referred to as "first invention" in the following description.)

The term "ppm" is used as meaning ppm by weight (wtppm) throughout the invention.

Further, it has been found that the above dehydration reaction takes place in a highly efficient and highly selective manner even if a ketone represented by General Formula (III) is present, without being accompanied by side reactions of the ketone.

[Chem. 1]

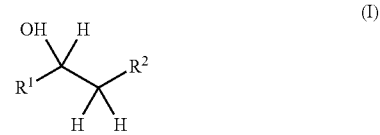

(I)

-continued

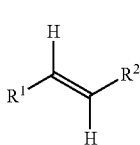
(II)

(In General Formulae (I) and (II), $R^1$ is a group selected from alkyl groups of 1 to 5 carbon atoms and aryl groups of 6 to 12 carbon atoms; and $R^2$ is an atom or a group selected from a hydrogen atom, alkyl groups of 1 to 5 carbon atoms and aryl groups of 6 to 12 carbon atoms.)

[Chem. 2]

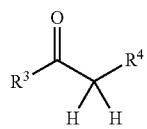
(III)

(In General Formula (III), $R^3$ is a group selected from alkyl groups of 1 to 5 carbon atoms and aryl groups of 6 to 12 carbon atoms; and $R^4$ is an atom or a group selected from a hydrogen atom, alkyl groups of 1 to 5 carbon atoms and aryl groups of 6 to 12 carbon atoms.)

As a result, the present inventors have found that it is now possible to produce an olefin represented by General Formula (II) in one stage in a highly active and highly selective manner by performing a hydrogenation reaction and a dehydration reaction of a ketone represented by General Formula (III) and hydrogen as starting materials in a single reaction step in the presence of a silver-containing inorganic substance (B), which has been disclosed as a hydrogenation catalyst by the present applicant (Patent Literature 3), and the silica gel (A) serving as a dehydration catalyst. (This invention is sometimes referred to as "second invention" in the following description.) In the second invention, $R^3$ in General Formula (III) and $R^1$ in General Formula (II) are the identical groups, and $R^4$ in General Formula (III) and $R^2$ in General Formula (II) are the identical atoms or groups.

In the invention, it is preferable that the silica gel (A) be a silica gel (A1) which is obtained by bringing a silica gel (X) prepared from an alkyl orthosilicate into contact with a water-soluble aluminum compound and calcining the contact product and which contains an aluminum compound at 10 to 1000 ppm in terms of aluminum element as well as an alkali metal and an alkaline earth metal at a total of 0 to 20 ppm.

In the invention, it is also preferable that the silica gel (A) be a silica gel (A2) which is obtained by chemically treating a wet-process silica gel (Y) prepared from an alkali silicate and which contains an aluminum compound at 10 to 1000 ppm in terms of aluminum element as well as an alkali metal and an alkaline earth metal at a total of 1 to 350 ppm. In detail, the silica gel (A2) is preferably any of the following silica gels (A2-1) to (A2-4).

(1) A silica gel (A2-1) is obtained by subjecting a wet-process silica gel (Y) prepared from an alkali silicate to a contact treatment with an acidic aqueous solution having a pH of 0.5 to less than 7, and calcining the product.

(2) A silica gel (A2-2) is obtained by bringing a wet-process silica gel (Y) prepared from an alkali silicate into contact with a water-soluble aluminum compound, and calcining the contact product.

(3) A silica gel (A2-3) is obtained by subjecting a wet-process silica gel (Y) prepared from an alkali silicate to a contact treatment with an acidic aqueous solution having a pH of 0.5 to less than 7, then bringing the product into contact with a water-soluble aluminum compound, and calcining the contact product.

(4) A silica gel (A2-4) is obtained by bringing a wet-process silica gel (Y) prepared from an alkali silicate into contact with a water-soluble aluminum compound, then subjecting the contact product to a contact treatment with an acidic aqueous solution having a pH of 0.5 to less than 7, and calcining the product.

It has been also found that in the second invention, in particular, propylene can be produced with high selectivity in a single reaction step using acetone as the ketone and hydrogen as starting materials.

In the second invention, it is preferable that the silver-containing inorganic substance (B) contain at least one Group 13 (IIIA) element in the periodic table.

In the second invention, the reaction is preferably carried out in the presence of a mixture of the silica gel (A) and the silver-containing inorganic substance (B).

In the first invention and the second invention, the reaction temperature is preferably 50 to 500° C.

Advantageous Effects of Invention

According to the method of the present invention, an olefin can be produced with high efficiency by selectively inducing a dehydration reaction of an alcohol even in the presence of a ketone without the occurrence of side reactions such as the Aldol condensation of the ketone.

Further, the method of the invention can produce an olefin in a single reaction step from a ketone and hydrogen as starting substances. In particular, the method is useful for obtaining propylene with high selectivity by directly reacting acetone and hydrogen. Thus, the method can be effectively incorporated into a recycle and reuse process for acetone that is by-produced by the cumene process. Because the reaction is accomplished in one step, the inventive method does not entail operations such as separation of intermediates and purification which are required in a method involving a plurality of reaction steps. Further, the inventive method can afford propylene with high purity.

DESCRIPTION OF EMBODIMENTS

The olefin production method of the present invention is characterized in that a dehydration catalyst is a chemically treated silica gel (A) which contains an aluminum compound at 10 to 1000 ppm, preferably 10 to 800 ppm, and more preferably 20 to 800 ppm in terms of aluminum element as well as an alkali metal and an alkaline earth metal at a total of 0 to 350 ppm, preferably 1 to 300 ppm, and more preferably 2 to 280 ppm.

The term "dehydration" used in the invention is defined to mean a reaction in which a hydrogen atom and a hydroxyl group on adjacent carbon atoms in the molecule are removed as a water molecule. Any terms including this word at the beginning or end are understood in a similar manner. In the invention, the term "dehydration" is sometimes referred to as "intramolecular dehydration".

In the invention, the term "chemical treatment" is defined to mean that a silica gel material is contacted with an acidic aqueous solution and/or a water-soluble aluminum compound. The water-soluble aluminum compound is usually used as an aluminum compound-containing aqueous solution. The contact is usually performed by solid-liquid contact. In detail, the silica gel (A) in the present invention is prepared by a solid-liquid contact treatment of a silica gel material (preferably a silica gel (X) or a silica gel (Y) as described later) and the aqueous solution(s).

The silica gel material to be chemically treated is any of silica gels that are produced by any of the six methods described in Jikken Kagaku Koza (Courses in Experimental Chemistry) 9, Mukikagoubutsu no Gousei to Seisei (Synthesis and Purification of Inorganic Compounds) (published on Dec. 20, 1958, MARUZEN PUBLISHING CO., LTD.), p. 513. Preferably, the silica gel material may be a silica gel (X) or a silica gel (Y) described later.

In the invention, the content of an aluminum compound is expressed in terms of aluminum element. In detail, the content of an aluminum compound is expressed in terms of the content of aluminum element present in the aluminum compound, and does not represent the amount of the aluminum compound in the silica gel (A).

In a preferred embodiment, the silica gel (A) is a silica gel (A1) which is obtained by bringing a silica gel (X) prepared from an alkyl orthosilicate into contact with a water-soluble aluminum compound and calcining the contact product and which contains an aluminum compound at 10 to 1000 ppm in terms of aluminum element as well as an alkali metal and an alkaline earth metal at a total of 0 to 20 ppm; or a silica gel (A2) which is obtained by chemically treating a wet-process silica gel (Y) prepared from an alkali silicate and which contains an aluminum compound at 10 to 1000 ppm in terms of aluminum element as well as an alkali metal and an alkaline earth metal at a total of 1 to 350 ppm.

The first invention is directed to an olefin production method in which an alcohol is caused to undergo an intramolecular dehydration reaction using the silica gel (A) as an essential catalyst so as to form the corresponding olefin. The second invention is directed to an olefin production method in which the silica gel (A) and a known silver-containing inorganic substance (B) are used in combination to catalyze reactions of a ketone and hydrogen to directly afford the corresponding olefin in a single reaction step. Hereinbelow, the first invention and the second invention will be sequentially described in detail.

First Invention

In the olefin production method of the first invention, an olefin represented by General Formula (II) below is produced with high activity and high selectivity from an alcohol of General Formula (I) below using a dehydration catalyst that is a chemically treated silica gel (A) containing an aluminum compound at 10 to 1000 ppm, preferably 10 to 800 ppm, and more preferably 20 to 800 ppm in terms of aluminum element as well as an alkali metal and an alkaline earth metal at a total of 0 to 350 ppm, preferably 1 to 300 ppm, and more preferably 2 to 280 ppm.

[Chem. 3]

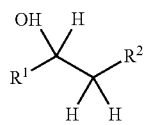

(I)

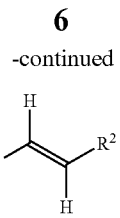

(II)

In General Formulae (I) and (II), $R^1$ is a group selected from alkyl groups of 1 to 5 carbon atoms and aryl groups of 6 to 12 carbon atoms; and $R^2$ is an atom or a group selected from a hydrogen atom, alkyl groups of 1 to 5 carbon atoms and aryl groups of 6 to 12 carbon atoms.

Examples of the alkyl groups of 1 to 5 carbon atoms that may be represented by $R^1$ and $R^2$ include methyl group, ethyl group, n-propyl group, isopropyl group, n-butyl group, s-butyl group, t-butyl group and n-amyl group. Examples of the aryl groups of 6 to 12 carbon atoms that may be represented by $R^1$ and $R^2$ include phenyl group, o-tolyl group, m-tolyl group, p-tolyl group, xylyl group and naphthyl group.

From the viewpoints of reaction results and easiness in separating the product, $R^1$ is preferably an alkyl group of 1 to 5 carbon atoms, and $R^2$ is preferably an atom or a group selected from a hydrogen atom and alkyl groups of 1 to 5 carbon atoms.

In a more preferred embodiment of the first invention, $R^1$ is a methyl group and $R^2$ is a hydrogen atom. Such an embodiment is more preferable because, as will be described later, the method can be directly applied to a process in which isopropyl alcohol obtained by the hydrogenation of acetone that is by-produced in the cumene process is caused to undergo intramolecular dehydration to reproduce propylene for use as a material in the cumene process.

According to the first invention, the dehydration reaction of an alcohol represented by General Formula (I) is allowed to take place efficiently while minimally suppressing the occurrence of side reactions such as the Aldol condensation of ketones even in the case where a ketone represented by General Formula (III) below is present in the system in an amount in terms of weight that is 0.01 to 10 times the amount of the alcohol represented by General Formula (I).

[Chem. 4]

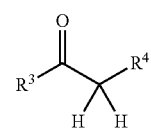

(III)

In General Formula (III), $R^3$ is a group selected from alkyl groups of 1 to 5 carbon atoms and aryl groups of 6 to 12 carbon atoms; and $R^4$ is an atom or a group selected from a hydrogen atom, alkyl groups of 1 to 5 carbon atoms and aryl groups of 6 to 12 carbon atoms.

Examples of the alkyl groups of 1 to 5 carbon atoms that may be represented by $R^3$ and $R^4$ include similar groups to the alkyl groups of 1 to 5 carbon atoms that may be represented by $R^1$ and $R^2$. Examples of the aryl groups of 6 to 12 carbon atoms that may be represented by $R^3$ and $R^4$ include similar groups to the aryl groups of 6 to 12 carbon atoms that may be represented by $R^1$ and $R^2$.

It is preferable that $R^3$ and $R^4$ in General Formula (III) be identical to $R^1$ and $R^2$ in General Formula (I), respectively.

In detail, it is preferable that $R^3$ and $R'$ be methyl groups, and $R^4$ and $R^2$ be hydrogen atoms. Such a configuration is preferable because even in the case where the hydrogenation reaction of acetone that is by-produced in the cumene process into isopropyl alcohol has not been completed, namely, even in the case where acetone is present in the system, the dehydration reaction of isopropyl alcohol is allowed to take place efficiently without being accompanied by side reactions such as the Aldol condensation of acetone, as well as because propylene can be produced from acetone and hydrogen in a single reaction step.

The dehydration catalyst used in the invention should function such that the catalyst does not participate in the Aldol condensation of a ketone, for example acetone, as described above, or in other reactions such as the oligomerization of an olefin such as propylene that is the target product, but the catalyst selectively catalyzes the dehydration reaction of a secondary alcohol such as isopropyl alcohol.

In a preferred embodiment of the dehydration catalyst satisfying the above requirements, the silica gel (A) of the invention is a silica gel (A1) which is obtained by bringing a silica gel (X) prepared from an alkyl orthosilicate into contact with a water-soluble aluminum compound and calcining the contact product and which contains an aluminum compound at 10 to 1000 ppm in terms of aluminum element as well as an alkali metal and an alkaline earth metal at a total of 0 to 20 ppm; or a silica gel (A2) which is obtained by chemically treating a wet-process silica gel (Y) prepared from an alkali silicate and which contains an aluminum compound at 10 to 1000 ppm in terms of aluminum element as well as an alkali metal and an alkaline earth metal at a total of 1 to 350 ppm. The silica gel (A1) and the silica gel (A2) will be described below.

[Silica Gel (A1)]

From the viewpoint of the efficiency in the dehydration reaction, the content of an aluminum compound in the silica gel (A1) is 10 to 1000 ppm, preferably 10 to 800 ppm, and more preferably 20 to 500 ppm in terms of aluminum element.

The silica gel (A1) of the invention is also characterized in that it contains an alkali metal and an alkaline earth metal at a total of 0 to 20 ppm, preferably 2 to 15 ppm, and more preferably more than 2 ppm and less than 10 ppm. This content ensures that the dehydration reaction of an alcohol proceeds effectively without the induction of side reactions of ketones.

The silica gel (A1) may be prepared by bringing a silica gel (X) into contact with a water-soluble aluminum compound, and drying and calcining the contact product. This silica gel (X) is obtained by hydrolyzing an alkyl orthosilicate, and aging, drying and calcining the hydrolyzate.

The basics of the preparation of the silica gel (X) from an alkyl orthosilicate are known. In EXAMPLES of the present invention, tetraethyl orthosilicate (hereinafter, sometimes abbreviated to TEOS) is used as the alkyl orthosilicate and is mixed with an alcohol and water by stirring in the presence of an acid to form a silica sol; the silica sol is aged by being allowed to stand for a prescribed time to give a gel; and the gel is dried and calcined to give a silica gel (X). In order to obtain a silica gel (X) having a uniform particle diameter, it is important to provide, during the course of preparation, a step in which water weighing 0.1 to 5 times the weight of TEOS is added to the system before drying to produce swelling.

The silica gel (X) obtained by the above method is brought into contact with an aqueous solution of a water-soluble aluminum compound, then water is distilled away, and the residue is dried and calcined. In this manner, a silica gel (A1) of the present invention is easily prepared. Examples of the water-soluble aluminum compounds include aluminum nitrate, aluminum sulfate and aluminum hydroxide, but are not limited thereto. In EXAMPLES of the present invention, aluminum nitrate is used as the water-soluble aluminum compound in the form of an aqueous solution having a low concentration of 0.1% by weight or 1.0% by weight and is brought into contact and mixed with the silica gel (X) in the presence of water; thereafter water is removed under reduced pressure; and the residue is dried at 120° C. and calcined at 500° C. to give a silica gel (A1) containing an alkali metal and an alkaline earth metal in a specific amount as well as an aluminum compound at a specific concentration. Performing the treatment step(s) at a high temperature as described above is preferable because such a treatment causes a change in surface condition and often leads to the suppression of side reactions.

[Silica Gel (A2)]

The silica gel (A2) is obtained by chemically treating a wet-process silica gel (Y) prepared from an alkali silicate as a material, and contains an aluminum compound at 10 to 1000 ppm in terms of aluminum element as well as an alkali metal and an alkaline earth metal at a total of 1 to 350 ppm.

From the viewpoint of the efficiency in the dehydration reaction, the content of an aluminum compound in the silica gel (A2) is usually 10 to 1000 ppm, preferably 10 to 500 ppm, and more preferably 10 to 400 ppm in terms of aluminum element. The total content of alkali metals and alkaline earth metals in the silica gel (A2) is 1 to 350 ppm, preferably 2 to 300 ppm, and more preferably 2 to 280 ppm. This content in the range is preferable because such a catalyst exhibits high alcohol conversion and high olefin selectivity in the dehydration reaction of the invention as well as because side reactions of ketones are suppressed even when a ketone is present in the reaction system. In some cases, the silica gel (A2) can contain a metal such as iron, titanium or zirconium derived from the alkali silicate as the material in an amount in the range of about 20 ppm to 200 ppm. However, it has been confirmed that the amounts of these metals do not substantially affect results of the reaction of interest in the present invention.

The silica gel (A2) may be prepared by any method without limitation as long as the silica gel (A2) is obtained by a chemical treatment of a wet-process silica gel prepared from an alkali silicate as a material. Preferably, the silica gel (A2) is any of the following silica gels (A2-1) to (A2-4).

Silica Gel (A2-1):

The silica gel (A2-1) is obtained by subjecting a wet-process silica gel (Y) prepared from an alkali silicate to a contact treatment with an acidic aqueous solution having a pH of 0.5 to less than 7, and calcining the product.

The wet-process silica gel (Y) may be prepared in accordance with a known method by hydrolyzing an alkali silicate such as silicate of soda with a mineral acid, and gelling and drying the resultant silica hydrosol. Alternatively, the wet-process silica gel (Y) may be commercially purchased. The wet-process silica gel (Y) is contact treated with an acidic aqueous solution having a pH of 0.5 to less than 7, washed with water as required and calcined to give the target silica gel. Examples of commercially available wet-process silica gels (Y) include CARiACT manufactured by Fuji Silysia Chemical Ltd., SUNSPHERE manufactured by AGC Si-Tech Co., Ltd., Nipgel manufactured by Tosoh Silica Corporation, and Carplex manufactured by DSL Japan. Examples of the acidic aqueous solutions having a pH of 0.5 to less than 7 include aqueous solutions of mineral acids such as hydrochloric acid, nitric acid and sulfuric acid, and aqueous solutions of organic acids such as formic acid, acetic acid, propionic acid, butyric acid, valeric acid, oxalic acid, malonic acid, succinic acid, fumaric acid, maleic acid and citric acid. Of these, an aqueous acetic acid solution is preferable in terms of economic efficiency. The wet-process silica gel (Y) is usually contact treated with the acidic aqueous solution at a temperature in the range of room temperature to 150° C., preferably 50 to 100° C., for 10 minutes to 5 hours. After the completion of the contact treatment, the acidic aqueous solution is separated by filtration, and the residue is washed with water as required and is subsequently dried and calcined to give the target silica gel. The drying temperature is 70 to 150° C., and preferably 80 to 130° C. The calcination temperature is 200 to 800° C., and preferably 200 to 700° C. In the invention, a series of steps from the contact treatment with the acidic aqueous solution to the calcination may be optionally carried out plural times.

Silica Gel (A2-2):

The silica gel (A2-2) is obtained by bringing a wet-process silica gel (Y) prepared from an alkali silicate into contact with a water-soluble aluminum compound, and calcining the contact product. In a usual embodiment, this silica gel is easily produced by a method in which a wet-process silica gel (Y) prepared from an alkali silicate is brought into contact with an aqueous solution of a water-soluble aluminum compound, then water is distilled away, and the residue is dried and calcined. In EXAMPLES of the present invention, aluminum nitrate is used as the water-soluble aluminum compound in the form of an aqueous solution having a low concentration of about 0.05 to 2.0% by weight and is brought into contact and mixed with the silica gel (Y) in the presence of water; thereafter water is removed under reduced pressure; and the residue is dried at 120° C. and calcined at 500° C. to give a silica gel (A2-2) which does not substantially contain an alkali metal or an alkaline earth metal and contains an aluminum compound at a specific concentration. Performing the calcination treatment step at a high temperature of 500° C. as described above is preferable because such a treatment causes a change in surface condition and often leads to the suppression of side reactions.

Silica Gel (A2-3):

The silica gel (A2-3) is obtained by subjecting a wet-process silica gel (Y) prepared from an alkali silicate to a contact treatment with an acidic aqueous solution having a pH of 0.5 to less than 7, then bringing the product into contact with a water-soluble aluminum compound, and calcining the contact product. A calcination treatment step may be optionally performed after the contact treatment with an acidic aqueous solution and before the contact with a water-soluble aluminum compound. The contact treatment with an acidic aqueous solution having a pH of 0.5 to less than 7, and the calcination may be carried out in accordance with the conditions described with respect to the preparation of the silica gel (A2-1). The contact with a water-soluble aluminum compound may be carried out in accordance with the conditions described with respect to the preparation of the silica gel (A2-2).

Silica Gel (A2-4):

The silica gel (A2-4) is obtained by bringing a wet-process silica gel (Y) prepared from an alkali silicate into contact with a water-soluble aluminum compound, then subjecting the contact product to a contact treatment with an acidic aqueous solution having a pH of 0.5 to less than 7, and calcining the product. A calcination treatment step may be optionally performed after the contact with a water-soluble aluminum compound and before the contact treatment with an acidic aqueous solution. The contact treatment with an acidic aqueous solution having a pH of 0.5 to less than 7, and the calcination may be carried out in accordance with the conditions described with respect to the preparation of the silica gel (A2-1). The contact with a water-soluble aluminum compound may be carried out in accordance with the conditions described with respect to the preparation of the silica gel (A2-2).

The shapes of the silica gel (A1) and the silica gel (A2) as the dehydration catalysts are not particularly limited and may be any of spheres, cylindrical columns, extrudates and crushed forms. The size of the catalyst particles may be selected in the range of 0.01 mm to 100 mm in accordance with the size of a reactor.

The reaction temperature in the first invention is not particularly limited, but is preferably in the range of 50 to 500° C., and more preferably 60 to 400° C. A preferred pressure in carrying out the reaction is usually 0.1 to 500 atm, and more preferably 0.5 to 100 atm.

Second Invention

The second invention is directed to an olefin production method in which an olefin represented by General Formula (II) below is produced from a ketone of General Formula (III) below and hydrogen in a single reaction step in the presence of the aforementioned chemically treated silica gel (A) containing an aluminum compound at 10 to 1000 ppm in terms of aluminum element as well as an alkali metal and an alkaline earth metal at a total of 0 to 350 ppm, and a silver-containing inorganic substance (B).

[Chem. 5]

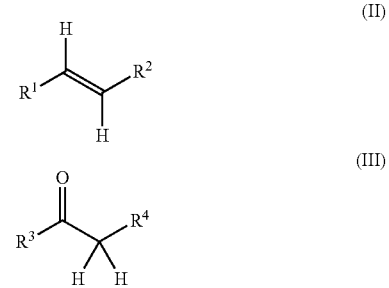

$R^1$ and $R^2$ in General Formula (II) are of the same definition as $R^1$ and $R^2$ described with respect to General Formulae (I) and (II) in the first invention. $R^3$ and $R^4$ in General Formula (III) are of the same definition as $R^3$ and $R^4$ described with respect to General Formula (III) in the first invention.

In the second invention, $R^3$ in General Formula (III) and $R^1$ in General Formula (II) are the identical groups, and $R^4$ in General Formula (III) and $R^2$ in General Formula (II) are the identical atoms or groups.

In the second invention, two components are used as catalysts, which are the silica gel (A) containing an aluminum compound at 10 to 1000 ppm in terms of aluminum element as well as an alkali metal and an alkaline earth metal at a total of 0 to 350 ppm, and a silver-containing inorganic substance (B). The catalyst components may be used in any manner without limitation. In an embodiment, the silica gel (A) and the silver-containing inorganic substance (B) may be physically mixed on a catalyst particle level with a centimeter size. Alternatively, these components may be finely pulverized and mixed together, and the mixture may be shaped into catalyst particles with a centimeter size. Still alternatively, the catalyst used herein may be such that the silica gel (A) is used as a carrier, and silver is supported thereon; or such that the silver-containing inorganic substance (B) is used as a carrier, and an aluminum compound is supported thereon.

In the olefin production method according to the invention (the second invention), it is considered that the silver-containing inorganic substance (B) acts as a hydrogenation catalyst to catalyze the hydrogenation of the ketone into an alcohol and thereafter the silica gel (A) as a dehydration catalyst catalyzes the dehydration reaction of the alcohol into an olefin. In the case where the olefin is propylene as an example, it is considered that acetone is hydrogenated into isopropyl alcohol under the catalysis of the silver-containing inorganic substance (B) and the isopropyl alcohol is caused to undergo a dehydration reaction by the action of the silica gel (A) as the dehydration catalyst to form propylene and water.

That is, it is considered that the hydrogenation reaction and the dehydration reaction take place stepwise in the olefin production method of the invention (the second invention). Accordingly, the catalysts may form distinct catalyst layers, namely, the appropriate catalyst species may be packed in sequence in accordance with the stages of the reactions. Alternatively, the silver-containing inorganic substance (B) and the silica gel (A) may be mixed together in a graded mixing ratio.

The ketone used in the invention may be selected appropriately in accordance with the desired olefin. For example, acetone is used as the ketone in order to produce propylene as the olefin, and methyl ethyl ketone is used as the ketone in order to obtain 1-butene as the olefin.

The olefin production method of the second invention is suitably used in a process in which acetone is used as the ketone to produce propylene as the olefin.

The material ketone is not particularly limited. For example, acetone that is by-produced in the production of phenol by the cumene process, or methyl ethyl ketone from the dehydrogenation of 2-butanol may be used. Further, the ketone may be any of various ketones obtained by the ozonolysis of olefins, or by the hydration reaction or the Friedel-Crafts alkanoylation of alkynes.

The hydrogen to be reacted with the ketone in the second invention may be molecular hydrogen gas or a hydrocarbon such as cyclohexane that generates hydrogen when subjected to specific reaction conditions. From the stoichiometric point of view, at least an equimolar amount of hydrogen relative to the ketone is sufficient. From the viewpoint of separation and recovery, the hydrogen may be preferably used in a 1 to 30-fold molar amount, and more preferably in a 1 to 15-fold molar amount relative to 1 mol of the ketone. When the ketone conversion is desired to be less than 100%, the hydrogen amount may be controlled to be less than the equimolar amount relative to the ketone. In the reaction of this invention, the hydrogen reacts with the carbonyl oxygen atom in the ketone and finally forms water, which may be recovered from a reactor outlet. An excess of hydrogen over the equivalent weight of the ketone is not essentially consumed as long as undesirable side reactions do not take place.

The hydrogen gas is generally supplied to the reaction system continuously, but the supply methods are not particularly limited thereto. In an embodiment, the hydrogen gas may be supplied intermittently such that the hydrogen gas is supplied at the initiation of the reaction and the supply is suspended during the reaction and restarted after a prescribed time. In the case of a liquid-phase reaction, the hydrogen gas may be supplied while being dissolved in a solvent. In a recycle process, hydrogen gas recovered from the column top together with low-boiling fractions may be recycled into the reaction system. The pressure of the supplied hydrogen is usually equal to the pressure in the reactor, but may be appropriately adjusted depending on the hydrogen supply method.

The contact between the reaction materials, i.e., the ketone and the hydrogen gas, may take place in a gas-liquid countercurrent flow or a gas-liquid co-current flow. The liquid and gas directions may be descending liquid/ascending gas, ascending liquid/descending gas, ascending liquid/ascending gas, or descending liquid/descending gas.

Hereinbelow, the dehydration catalyst and the hydrogenation catalyst used in the second invention will be described.

⟨Dehydration Catalyst⟩

The dehydration catalyst in the second invention may be the chemically treated silica gel (A) used in the first invention which contains an aluminum compound at 10 to 1000 ppm in terms of aluminum element as well as an alkali metal and an alkaline earth metal at a total of 0 to 350 ppm. This chemically treated silica gel (A) may be used as such directly.

⟨Hydrogenation Catalyst⟩

A silver-containing inorganic substance (B) is used as the hydrogenation catalyst in the second invention. In the invention, the silver-containing inorganic substance (B) is not particularly limited as long as it is an inorganic substance (B) containing silver element in the substance and functions as a hydrogenation catalyst.

The silver-containing inorganic substances (B) may be used singly, or two or more kinds may be used in combination.

The silver-containing inorganic substance (B) used as the hydrogenation catalyst in the invention catalyzes the hydrogenation of ketones, but does not substantially function as a hydrogenation catalyst for olefins. Accordingly, the amounts of paraffins that are by-produced by the hydrogenation of olefins may be reduced compared to when the reaction is catalyzed by, for example, a copper-containing hydrogenation catalyst. For example, in the case where the ketone is acetone, the generation of by-product propane is suppressed by the use of the silver-containing inorganic substance as the hydrogenation catalyst.

In a preferred embodiment, the silver-containing inorganic substance (B) used as the hydrogenation catalyst further contains at least one Group 13 (IIIA) element in the periodic table. A typical example of the Group 13 (IIIA) elements is indium. In particular, the silver-containing inorganic substance (B) which further contains indium is preferable because the hydrogenation of the target olefin into a by-product paraffin can be suppressed more strongly.

Examples of the silver-containing inorganic substances (B) include silica gels that contain a silver compound in the form of $Ag_2O$ (metal oxide), AgCl (metal chloride) or a cluster metal such as Cu—Ag.

The silver-containing inorganic substance (B) usually has a configuration in which silver is supported on a carrier. Examples of the carriers include silica, alumina, silica alumina, titania, magnesia, silica magnesia, zirconia, zinc oxide, carbon, acid clay, diatomaceous earth and zeolite. In particular, at least one carrier is preferably selected from silica, alumina, silica alumina, titania, magnesia, silica magnesia, zirconia, zinc oxide and carbon. As demonstrated in EXAMPLES of the invention later, the silica gel (A) as the dehydration catalyst in the invention may be used as silica.

For example, the supported silver-containing inorganic substance (B) may be prepared by impregnating the carrier with an aqueous solution of a silver compound such as silver nitrate and calcining the impregnated carrier. Alternatively, silver may be bonded with an organic molecule ligand which makes silver soluble in an organic solvent, and the carrier may be impregnated with a solution of this complex in an organic solvent and thereafter calcined. Taking advantage of the fact that some complexes are vaporized under vacuum, such a complex may be supported on the carrier by deposition or the like. Further, a coprecipitation method may be adopted in which the carrier is obtained from a corresponding metal salt in the presence of silver element which will form the hydrogenation catalyst and thereby the carrier synthesis and the supporting of silver are carried out simultaneously. Furthermore, a commercially available silver-containing silica gel or the like may be used. The silver-containing inorganic substances (B) may be used singly, or two or more kinds may be used in combination.

In the case where the silver-containing inorganic substance (B) further contains at least one Group 13 (IIIA) element in the periodic table, such a catalyst may be prepared by, for example, supporting a Group 13 (IIIA) element on a catalyst containing silver element.

In some cases, the addition of metal salts such as $PbSO_4$, $FeCl_2$ and $SnCl_2$, or other salts such as $BaSO_4$ to the silver-containing inorganic substance (B) improves the activity and selectivity in the hydrogenation of ketones. Thus, these salts may be added as required.

The shape of the silver-containing inorganic substance (B) is not particularly limited and may be any of spheres, cylindrical columns, extrudates and crushed forms. The size of the catalyst particles may be selected in the range of 0.01 mm to 100 mm in accordance with the size of a reactor.

As described above, the silver-containing inorganic substance (B) may be supported on the silica gel (A) as the dehydration catalyst. For example, such a supported silver-containing inorganic substance (B) may be prepared by impregnating the silica gel (A) with an aqueous solution of silver nitrate or the like and calcining the impregnated product. Alternatively, silver may be bonded with an organic molecule ligand which makes silver soluble in an organic solvent, and the silica gel (A) may be impregnated with a solution of this complex in an organic solvent and thereafter calcined. Taking advantage of the fact that some complexes are vaporized under vacuum, such a complex may be supported on the silica gel (A) by deposition or the like. Further, a coprecipitation method may be adopted in which the silica gel (A) is obtained from a corresponding metal salt in the presence of silver element which will form the silver-containing catalyst and thereby the carrier synthesis and the supporting of the silver-containing catalyst are carried out simultaneously.

The reaction temperature in the second invention is not particularly limited, but is preferably in the range of 50 to 500° C., and more preferably 60 to 400° C. A preferred pressure in carrying out the reaction is usually 0.1 to 500 atm, and more preferably 0.5 to 100 atm.

The amount of the catalysts in carrying out the second invention is not particularly limited. In an embodiment in which the reaction is performed in a fixed bed flow apparatus, the catalyst amount may be preferably such that the supply amount (weight) of the starting material (ketone) per hour divided by the catalyst weight (the total weight of the silver-containing catalyst and the dehydration catalyst), namely, WHSV is in the range of 0.01 to 200/h, and more preferably 0.02 to 100/h.

The ratio of the amounts of the silica gel (A) as the dehydration catalyst and the silver-containing inorganic substance (B) as the hydrogenation catalyst is not particularly limited. However, the silica gel (A):silver-containing inorganic substance (B) (weight ratio) is usually 1:0.01 to 1:100, and preferably 1:0.05 to 1:50. An excessively small weight ratio of the dehydration catalyst results in insufficient dehydration reaction and a decrease in the olefin yield, causing economic disadvantages. An excessively large weight ratio of the dehydration catalyst is uneconomical because the ketone conversion is lowered.

In the second invention, the dehydration catalyst and the hydrogenation catalyst are used as a mixture. In the case where the reaction mode is a fixed bed reaction, the manner of packing the catalysts can greatly affect the reaction results. As described hereinabove, the hydrogenation and the dehydration are considered to take place stepwise in the second invention. Accordingly, the appropriate catalyst species are preferably packed in sequence in accordance with the stages of the reactions in order to catalyze the reactions efficiently and suppress undesired side reactions.

In general, chemical reactions frequently behave such that undesired side reactions that are not observed at a lower hydrogen pressure or a lower temperature take place when, in particular, the hydrogen pressure or the temperature is increased to accelerate the reaction rate. In such cases, the reaction results can be greatly influenced by how the catalysts are packed, and therefore an appropriate packing manner such as a packing manner (2) described later is preferably adopted.

Exemplary manners for packing the catalyst species include: (1) the silica gel (A) and the silver-containing inorganic substance (B) are mixed together and the mixture is packed in the reactor; (2) the silver-containing inorganic substance (B) is packed to form a layer (on the upstream side), and the silica gel (A) is packed to form a layer (on the downstream side); (3) the silica gel (A) supporting the silver-containing inorganic substance (B) is packed in the reactor; (4) the silver-containing inorganic substance (B) is packed to form a layer (on the upstream side), and the silica gel (A) and the silver-containing inorganic substance (B) are packed together to form a layer (on the downstream side); (5) the silver-containing inorganic substance (B) is packed to form a layer (on the upstream side), and the silica gel (A) supporting the silver-containing inorganic substance (B) is packed to form a layer (on the downstream side); (6) the silica gel (A) and the silver-containing inorganic substance (B) are packed together to form a layer (on the upstream side), and the silica gel (A) is packed to form a layer (on the downstream side); and (7) the silica gel (A) supporting the silver-containing inorganic substance (B) is packed to form a layer (on the upstream side), and the silica gel (A) is packed to form a layer (on the downstream side). Here, the term upstream side means the inlet side of a reactor, namely, a layer through which the materials are passed in the first half of the reactions. The term downstream side means the outlet side of a reactor, namely, a layer through which the materials are passed in the last half of the reactions. In the case where the reactions are performed by bringing the ketone and hydrogen into contact with each other in a gas-liquid countercurrent flow, the inlet side of a reactor indicates an inlet for introducing the ketone.

In carrying out the first invention and the second invention, the reactions may be performed in a diluted reaction system by adding a solvent or gas that is inert to the catalysts and the reagents.

In carrying out the first invention and the second invention, the method may be a batch method, a semi-batch method or a continuous flow method. The reaction phase may be a liquid phase, a gas phase or a gas-liquid mixed phase. The catalyst packing system may be any of various systems including fixed bed systems, fluidized bed systems, suspended bed systems and multistage fixed bed systems. The methods of the invention may be carried out with any of these systems.

In carrying out the second invention, the silica gel (A) as the dehydration catalyst and the silver-containing inorganic substance (B) as the hydrogenation catalyst may be dried by removing water by a known method. In the case of a fixed bed reaction mode, the silica gel (A) and the silver-containing inorganic substance (B) may be dried by being held at a temperature of 300° C. or above for at least 10 minutes while passing an inert gas such as nitrogen or helium through the reactor packed with these catalysts. In order to allow the silver-containing catalyst to exhibit activity, a treatment under a stream of hydrogen may be performed after the drying treatment for water removal.

In the event that the catalyst activity is lowered after a passage of time, the dehydration catalyst and the silver-containing catalyst may be regenerated by a known method to recover the activities.

In order to maintain the olefin output, two or three reactors may be arranged in parallel to realize a merry-go-round system in which the catalysts in one reactor are regenerated while the reaction is continuously carried out in the remaining one or two reactors. When three reactors are available, two of the reactors may be connected in series to reduce variations in output. When the method is carried out in a fluidized bed flow reaction mode or in a moving bed reaction mode, part or the whole of the catalysts may be withdrawn from the reactor continuously or intermittently while a corresponding amount of the catalysts is newly added to maintain the activities at a constant level.

In the case where the second invention is carried out in the presence of an aromatic compound such as benzene, an alkylated benzene may be obtained. In detail, an alkylated aromatic compound such as cumene may be effectively obtained in a single reaction step using a ketone such as acetone, an aromatic compound such as benzene, and hydrogen as starting materials.

EXAMPLES

The present invention will be described in detail by presenting examples hereinbelow without limiting the scope of the invention.

[Method 1 for Evaluating Dehydration Catalyst]

In order to evaluate the activity of a dehydration catalyst in dehydrating isopropyl alcohol (hereinafter, sometimes abbreviated to IPA) and the reactivity of acetone side reactions, a normal pressure downflow reaction was carried out in the following manner using a fixed bed reaction apparatus which included a feed pump, a nitrogen line, an electric furnace, a reaction liquid collection unit and a reactor having a catalyst-packing zone.

One gram of a dehydration catalyst classified to sizes of 250 to 500 μm was packed into a SUS 316 reactor having an inner diameter of 1 cm. While passing nitrogen at 10 ml/min from the top of the reactor, the temperature of the catalyst layer was elevated to 300° C. by heating. A reaction was performed by passing a solution which contained equimolar amounts of acetone and IPA as reaction materials through the reactor at 2 ml/h. After the passage of 5 hours from the initiation of liquid passage, the reaction gas and the reaction liquid were sampled and analyzed by GC (gas chromatography), thereby calculating the reaction results.

[Method 2 for Evaluating Dehydration Catalyst]

In order to evaluate the activity of a dehydration catalyst in dehydrating IPA and the reactivity of acetone side reactions, a pressurized liquid-phase downflow reaction was carried out in the following manner using a fixed bed reaction apparatus which included a high pressure liquid feed pump, a high pressure hydrogen mass flow controller, a high pressure nitrogen mass flow controller, an electric furnace, a reactor having a catalyst-packing zone, and a back pressure valve.

One gram of a dehydration catalyst classified to sizes of 250 to 500 μm was packed into a SUS 316 reactor having an inner diameter of 1 cm. After the pressure was increased to 3.0 MPa with hydrogen, a solution which contained equimolar amounts of acetone and IPA was passed through the reactor at 1.6 g/h and 300° C. under a stream of hydrogen at 10 ml/min from the inlet side of the reactor. The reaction was carried out while introducing nitrogen at 50 ml/min in the middle between the reactor outlet and the back pressure valve through the high pressure nitrogen mass flow controller. After the passage of 5 hours from the initiation of liquid passage, the reaction gas and the reaction liquid were sampled from the exit side of the back pressure valve and were analyzed by GC, thereby calculating the reaction results.

Example 1

A 300 ml eggplant-shaped flask was charged with 30 g of an aqueous nitric acid solution adjusted to pH 3.1, 150 ml of ethyl alcohol and 69.5 g of tetraethyl orthosilicate (TEOS). These materials were stirred at 80° C. After a gel was formed, 100 ml of water was added. The gel that had swollen by containing water was dried at 120° C. and calcined at 500° C. to give 20 g of a silica gel. The silica gel was subjected to ICP metal analysis, which detected 2 ppm of aluminum element, 5 ppm of sodium, 2 ppm of calcium, 1 ppm of iron and 1 ppm of zinc. Thus, the total content of alkali metals (Group IA) and alkaline earth metals (Group IIA) was found to be 7 ppm. In the inductively-coupled plasma (ICP) analysis, the lower limit of quantification of metals is 1 ppm. In the following description, contents below the lower limit of quantification are indicated as "Not Detected (ND)".

Next, a 100 ml eggplant-shaped flask was charged with 3 g of the silica gel obtained above, 10 g of water and 1.25 g of a 0.1 wt % aqueous aluminum nitrate solution. These were stirred at room temperature for 1 hour. Excess water was removed under a reduced pressure. The residue was dried at 120° C. for 3 hours and calcined at 500° C. for 6 hours to give a silica gel (A1) as a dehydration catalyst according to the present invention. As a result of ICP metal analysis for the catalyst, 30 ppm of aluminum element was detected. The catalytic performance in dehydration of the catalyst was evaluated in accordance with the evaluation method 1. The results are described in Table 1.

Example 2

The procedures in Example 1 were repeated, except that 3 g of the silica gel prepared from TEOS, 10 g of water and 4.17 g of a 0.1 wt % aqueous aluminum nitrate solution were used, thereby preparing a silica gel (A1) supporting an aluminum compound at 100 ppm in terms of aluminum element.

The total content of alkali metals and alkaline earth metals was 7 ppm similarly to the content in the silica gel of Example 1. The catalytic performance in dehydration of the catalyst was evaluated in accordance with the evaluation method 1. The results are described in Table 1.

Example 3

The procedures in Example 1 were repeated, except that 3 g of the silica gel prepared from TEOS, 10 g of water and 2.08 g of a 1.0 wt % aqueous aluminum nitrate solution were used, thereby preparing a silica gel (A1) supporting an aluminum compound at 500 ppm in terms of aluminum element.

The total content of alkali metals and alkaline earth metals was 7 ppm similarly to the content in the silica gel of Example 1. The catalytic performance in dehydration of the catalyst was evaluated in accordance with the evaluation method 1. The results are described in Table 1.

Example 4

The procedures in Example 1 were repeated, except that 3 g of the silica gel prepared from TEOS, 10 g of water and 4.17 g of a 1.0 wt % aqueous aluminum nitrate solution were used, thereby preparing a silica gel (A1) supporting an aluminum compound at 1000 ppm in terms of aluminum element.

The total content of alkali metals and alkaline earth metals was 7 ppm similarly to the content in the silica gel of Example 1. The catalytic performance in dehydration of the catalyst was evaluated in accordance with the evaluation method 1. The results are described in Table 1.

Comparative Example 1

The silica gel prepared from TEOS in Example 1 was directly evaluated with respect to the catalytic performance in dehydration in accordance with the evaluation method 1. The reaction results are described in Table 1.

Comparative Example 2

The procedures in Example 2 were repeated, except that the 0.1 wt % aqueous aluminum nitrate solution was replaced by 6.25 g of a 1.0 wt % aqueous aluminum nitrate solution, thereby preparing a silica gel supporting an aluminum compound at 1500 ppm in terms of aluminum element.

The total content of alkali metals and alkaline earth metals was 7 ppm similarly to the content in the silica gel of Example 1. The catalytic performance in dehydration of the catalyst was evaluated in accordance with the evaluation method 1. The results are described in Table 1.

Example 5

The reaction was performed using the silica gel (A1) of Example 1 in the same manner as in Example 1, except that the equimolar solution of acetone and IPA used in the evaluation method 1 was replaced by an equimolar solution of methyl ethyl ketone (MEK) and isopropyl alcohol. The results are described in Table 1.

TABLE 1

|  | Metal contents (ppm) [Note 1] | | | | | Reaction results (mol %) | | |
| --- | --- | --- | --- | --- | --- | --- | --- | --- |
|  | Al | Na | Ca | Mg | IA + IIA | IPA conversion | Propylene selectivity | Acetone recovery rate |
| Ex. 1 | 30 | 5 | 2 | ND | 7 | 81.1 | 99.9 | 99.9 |
| Ex. 2 | 100 | 5 | 2 | ND | 7 | 99.9 | 99.5 | 99.2 |
| Ex. 3 | 500 | 5 | 2 | ND | 7 | 99.9 | 99.3 | 99.0 |
| Ex. 4 | 1000 | 5 | 2 | ND | 7 | 97.3 | 92.0 | 92.3 |
| Comp. Ex. 1 | 2 | 5 | 2 | ND | 7 | 0.4 | 97.0 | 99.0 |
| Comp. Ex. 2 | 1500 | 5 | 2 | ND | 7 | 98.1 | 85.3 | 87.1 |
| Ex. 5 | 30 | 5 | 2 | ND | 7 | 83.2 | 99.9 | 99.8 [Note 2] |

[Note 1] ND in the table indicates that the metal was not detected.
[Note 2] MEK was used instead of aceton in the experiment. The value indicates a MEK recovery rate (%) obtained by GC analysis.

From the results of Examples 1 to 4 and Comparative Examples 1 and 2 in Table 1, it has been shown that the silica gels (A1) as dehydration catalysts containing specific amounts of aluminum element, alkali metals and alkaline earth metals are excellent in terms of IPA conversion, propylene selectivity and acetone recovery rate which indicates how much of acetone has been consumed by side reactions such as Aldol reaction. Further, the results of Example 5 have shown that the dehydration reaction of IPA proceeds selectively even in the presence of a ketone which does not correspond to IPA, without any consumption of the ketone.

Example 6

A 300 ml eggplant-shaped flask was charged with 20 g of CARiACT (Q-10) manufactured by Fuji Silysia Chemical Ltd. and 100 g of a 5% aqueous acetic acid solution. These were stirred at 80° C. for 30 minutes, and the acetic acid solution was separated by filtration. The residual silica gel was combined with 100 g of a 5% aqueous acetic acid solution and was treated in the same manner. These operations were repeated three times. The silica gel separated from the acetic acid solution was washed with water, dried at 120° C. for 3 hours and calcined at 500° C. for 6 hours to give a silica gel (A2). The catalytic performance in dehydration of the catalyst was evaluated in accordance with the evaluation method 1. The reaction results are described in Table 2.

ICP metal analysis with respect to the catalyst detected 73 ppm of aluminum, 14 ppm of sodium, 34 ppm of magnesium and 74 ppm of calcium, as well as 37 ppm of iron, 130 ppm of titanium and 17 ppm of zirconium. In the inductively-coupled plasma (ICP) analysis, the lower limit of quantification of metals is 1 ppm. In the following Examples, contents below the lower limit of quantification are indicated as "Not Detected (ND)".

Example 7

The procedures in Example 6 were repeated, except that CARiACT (Q-10) manufactured by Fuji Silysia Chemical Ltd. was replaced by CARiACT (Q-3) manufactured by Fuji Silysia Chemical Ltd., and this silica gel was washed with acetic acid, dried and calcined in the same manner. The catalytic performance in dehydration of the thus-obtained silica gel (A2) was evaluated in accordance with the evaluation method 1. The reaction results are described in Table 2.

ICP metal analysis with respect to the catalyst detected 29 ppm of aluminum, 3 ppm of sodium, ND of magnesium and ND of calcium, as well as 25 ppm of iron, 96 ppm of titanium and 16 ppm of zirconium.

Example 8

The procedures in Example 7 were repeated, except that the 5% aqueous acetic acid solution was replaced by a 0.1N aqueous hydrochloric acid solution. The catalytic performance in dehydration of the thus-obtained silica gel (A2) was evaluated in accordance with the evaluation method 1. The reaction results are described in Table 2.

Example 9

The procedures in Example 7 were repeated, except that the 5% aqueous acetic acid solution was replaced by a 0.1N aqueous nitric acid solution. The catalytic performance in dehydration of the thus-obtained silica gel (A2) was evaluated in accordance with the evaluation method 1. The reaction results are described in Table 2.

Example 10

Twenty gram of the silica gel (A2) obtained in Example 6 was added to a 100 ml eggplant-shaped flask which contained 10 g of water and 13.9 g of a 0.1 wt % aqueous aluminum nitrate solution. These were stirred at room temperature for 1 hour. Excess water was removed under a reduced pressure. The residue was dried at 120° C. for 3 hours and calcined at 500° C. for 6 hours to give a silica gel (A2) supporting 50 ppm of aluminum. The catalytic performance in dehydration of the catalyst was evaluated in accordance with the evaluation method 1. The reaction results are described in Table 2.

Example 11

The silica gel (A2) obtained in Example 6 was treated in the same manner as in Example 10 so as to support aluminum on the silica gel. Thus, a silica gel (A2) supporting 250 ppm of aluminum was prepared. The catalytic performance in dehydration of the catalyst was evaluated in accordance with the evaluation method 1. The reaction results are described in Table 2.

Example 12

Ten gram of CARiACT (Q-10) manufactured by Fuji Silysia Chemical Ltd. was added to 34.7 g of a 0.1 wt % aqueous aluminum nitrate solution in a 300 ml eggplant-shaped flask. These were stirred at room temperature for 1 hour. Excess water was removed under a reduced pressure. The residue was dried at 120° C. for 3 hours and calcined at 500° C. for 6 hours to give a silica gel (A2) supporting 250 ppm of aluminum. The catalytic performance in dehydration of the catalyst was evaluated in accordance with the evaluation method 1. The reaction results are described in Table 2.

Example 13

Ten gram of CARiACT (Q-3) manufactured by Fuji Silysia Chemical Ltd. was added to a liquid consisting of 10 g of water and 13.9 g of a 0.1 wt % aqueous aluminum nitrate solution in a 300 ml eggplant-shaped flask. These were stirred at room temperature for 1 hour. Excess water was removed under a reduced pressure. The residue was dried at 120° C. for 3 hours and calcined at 500° C. for 6 hours to give a silica gel (A2) supporting 100 ppm of aluminum. The catalytic performance in dehydration of the catalyst was evaluated in accordance with the evaluation method 1. The reaction results are described in Table 2.

Comparative Example 3

The catalytic performance in dehydration of CARiACT (Q-10) manufactured by Fuji Silysia Chemical Ltd. was evaluated in accordance with the evaluation method 1. The reaction results are described in Table 2.

ICP metal analysis with respect to the catalyst detected 42 ppm of sodium, 77 ppm of magnesium and 150 ppm of calcium, as well as aluminum, iron, titanium and zirconium in the same concentrations as described in Example 6.

Comparative Example 4

The catalytic performance in dehydration of CARiACT (Q-3) manufactured by Fuji Silysia Chemical Ltd. was evaluated in accordance with the evaluation method 1. The reaction results are described in Table 2.

ICP metal analysis with respect to the catalyst detected 250 ppm of sodium, 1 ppm of magnesium and 5 ppm of calcium, as well as aluminum, iron, titanium and zirconium in the same concentrations as described in Example 7.

TABLE 2

| | Metal contents (ppm) | | | | | Reaction results (mol %) | | |
|---|---|---|---|---|---|---|---|---|
| | Al | Na | Ca | Mg | IA + IIA | IPA conversion | Propylene selectivity | Acetone recovery rate |
| Ex. 6 | 73 | 14 | 74 | 34 | 122 | 94.6 | 99.8 | 99.9 |
| Comp. Ex. 3 | 73 | 42 | 150 | 77 | 269 | 2.0 | 95.7 | — |
| Ex. 7 | 29 | 3 | ND | ND | 3 | 96.5 | 99.6 | 99.7 |
| Ex. 8 | 28 | 3 | ND | ND | 3 | 96.9 | 99.6 | 99.7 |
| Ex. 9 | 26 | 3 | ND | ND | 3 | 94.9 | 99.5 | 99.5 |
| Comp. Ex. 4 | 29 | 250 | 5 | 1 | 255 | 2.5 | 99.4 | — |
| Ex. 10 | 123 | 14 | 74 | 34 | 122 | 99.8 | 99.7 | 99.8 |
| Ex. 11 | 323 | 14 | 74 | 34 | 122 | 99.9 | 99.0 | 99.3 |
| Ex. 12 | 323 | 42 | 150 | 77 | 122 | 99.3 | 99.7 | 99.8 |
| Ex. 13 | 129 | 250 | 5 | 1 | 122 | 99.9 | 99.5 | 99.2 |

In the table, ND indicates that the metal was not detected, and "—" indicates that the analysis was not performed.

From Table 2, it has been shown that IPA conversion and propylene selectivity are improved by using the silica gels (A2) which are obtained by supporting aluminum on a commercial wet-process silica gel and/or which contain a specific total amount of alkali metals and alkaline earth metals as a result of the contact treatment with an acidic aqueous solution. The reason why the contents of alkali metals and alkaline earth metals in the commercial silica gel were decreased by the acid washing treatment is probably because the alkali metals and the alkaline earth metals were removed by being neutralized by the acid.

Comparative Example 5

The catalytic performance in dehydration of β-zeolite was evaluated in accordance with the evaluation method 1. The reaction results are described in Table 3.

Comparative Example 6

The catalytic performance in dehydration of γ-alumina was evaluated in accordance with the evaluation method 1. The reaction results are described in Table 3.

Comparative Example 7

The catalytic performance in dehydration of zirconia was evaluated in accordance with the evaluation method 1. The reaction results are described in Table 3.

Comparative Example 8

The catalytic performance in dehydration of hydrotalcite was evaluated in accordance with the evaluation method 1. The reaction results are described in Table 3.

Comparative Example 9

The catalytic performance in dehydration of titania was evaluated in accordance with the evaluation method 1. The reaction results are described in Table 3.

TABLE 3

| | Dehydration catalysts | Reaction results (mol %) | | |
|---|---|---|---|---|
| | | IPA conversion | Propylene selectivity | Acetone recovery rate |
| Comp. Ex. 5 | β-Zeolite | 99.9 | 85.0 | 86.0 |
| Comp. Ex. 6 | γ-Alumina | 97.2 | 86.2 | 88.1 |
| Comp. Ex. 7 | Zirconia | 79.3 | 56.5 | 57.8 |
| Comp. Ex. 8 | Hydrotalcite | 81.6 | 1.4 | 34.2 |
| Comp. Ex. 9 | Titania | 22.2 | 41.0 | 74.0 |

The reactions catalyzed by these known solid acid catalysts allegedly having a dehydrating function (Table 3) resulted in a decrease in propylene selectivity due to the oligomerization of propylene and the reaction between acetone molecules producing a large amount of by-products.

Example 14

The dehydration catalyst used in Example 6 was evaluated under high pressure conditions in accordance with the evaluation method 2. The reaction results are described in Table 4.

Example 15

The dehydration catalyst used in Example 10 was evaluated under high pressure conditions in accordance with the evaluation method 2. The reaction results are described in Table 4.

Example 16

The dehydration catalyst used in Example 11 was evaluated under high pressure conditions in accordance with the evaluation method 2. The reaction results are described in Table 4.

TABLE 4

| | Metal contents (ppm) | | | | | Time hr | Eval. Mthd. | Reaction results (mol %) | | |
|---|---|---|---|---|---|---|---|---|---|---|
| | Al | Na | Ca | Mg | IA + IIA | | | IPA conversion | Propylene selectivity | Acetone recovery rate |
| Ex. 14 | 73 | 14 | 74 | 34 | 122 | 117 | 2 | 96.5 | 99.4 | 99.5 |
| Ex. 15 | 123 | 14 | 74 | 34 | 122 | 137 | 2 | 99.3 | 98.6 | 98.9 |
| | | | | | | 306 | | 98.8 | 99.2 | 99.3 |
| Ex. 16 | 323 | 14 | 74 | 34 | 122 | 67 | 2 | 96.4 | 99.3 | 99.4 |
| | | | | | | 333 | | 97.9 | 99.4 | 99.5 |

From Table 4, it has been shown that the silica gels (A2) according to the invention afford propylene with high selectivity even under a stream of hydrogen gas at high pressure while suppressing a side reaction of acetone molecules.

Example 17

A 300 ml eggplant-shaped flask was charged with 50.0 g of a silica gel (Wakogel C-100 manufactured by Wako Pure Chemical Industries, Ltd.), 4.77 g of silver lactate (0.5 hydrate) and 100 ml of ion exchange water. These materials were mixed together using a rotary evaporator at room temperature for 1 hour. Water was distilled away at a reduced pressure of 20 mmHg at 40 to 50° C. Thus, silver was supported on the silica gel. The silver-supporting silica gel was subjected to a reduction treatment in which the temperature was increased stepwise from 100° C. to 300° C. in 5 hours under a stream of hydrogen. As a result, 52.5 g of a black 5% Ag/silica catalyst was obtained.

A 300 ml eggplant-shaped flask was charged with 29.1 g of the 5% Ag/silica catalyst, 0.86 g of indium nitrate trihydrate and 100 ml of ion exchange water. These materials were mixed together using a rotary evaporator at room temperature for 1 hour. Water was distilled away at a reduced pressure of 20 mmHg at 40 to 50° C. Thus, indium nitrate was supported on the 5% Ag/silica catalyst. The indium-supporting 5% Ag/silica catalyst was subjected to a reduction treatment in which the temperature was increased stepwise from 100° C. to 300° C. in 3 hours under a stream of hydrogen. As a result, 29.2 g of a black 5% Ag-1% In/silica catalyst was obtained. The 5% Ag-1% In/silica catalyst was sieved to sizes of 250 to 500 μm.

To form a catalyst layer, 6.0 g of the 5% Ag-1% In/silica catalyst obtained above and 1.0 g of a silica gel as a dehydration catalyst which had been prepared by the method described in Example 2 and supported an aluminum compound at 100 ppm in terms of aluminum element were mixed together sufficiently and packed into a SUS 316 reactor having an inner diameter of 1 cm. The total content of alkali metals and alkaline earth metals in the silica gel was 7 ppm similarly to the content in the silica gel prepared in Example 2.

The pressure was increased to 3.0 MPa with hydrogen. Under a stream of hydrogen at 22 ml/min, acetone was passed from the inlet side of the reactor at a rate of 0.30 g/h at 300° C.

Nitrogen was introduced at 50 ml/min in the middle between the reactor outlet and a back pressure valve through a high pressure nitrogen mass flow controller. Sampling was performed from a line located downstream from the back pressure valve, and the products were quantitatively determined by GC analysis. The reaction results are described in Table 5.

Comparative Example 10

The reaction was carried out in the same manner as described in Example 17, except that the dehydration catalyst used in Example 17 was replaced by the silica gel used in Comparative Example 1. The reaction results are described in Table 5.

Example 18

The reaction was carried out in the same manner as described in Example 17, except that the dehydration catalyst used in Example 17 was replaced by the silica gel used in Example 4 which supported an aluminum compound at 1000 ppm in terms of aluminum element. The reaction results are described in Table 5.

Example 19

A 300 ml eggplant-shaped flask was charged with 10.0 g of a silica gel prepared from TEOS as described in Example 1, 7.87 g of a 10 wt % aqueous silver nitrate solution and 20 ml of ion exchange water. These materials were mixed together using a rotary evaporator at room temperature for 1 hour. Water was distilled away at a reduced pressure of 20 mmHg at 40 to 50° C. Thus, silver was supported on the silica gel. The silver-supporting silica gel was subjected to a reduction treatment in which the temperature was increased stepwise from 100° C. to 300° C. in 5 hours under a stream of hydrogen. As a result, 10.5 g of a black 5% Ag/silica catalyst was obtained.

To form a catalyst layer, 1.5 g of the 5% Ag/silica catalyst obtained above and 1.5 g of a silica gel as a dehydration catalyst which had been prepared by the method described in Example 2 and supported an aluminum compound at 100 ppm in terms of aluminum element were mixed together sufficiently and packed into a reactor. The reaction was carried out in the same manner as in Example 17. The total content of alkali metals and alkaline earth metals in the silica gel was 7 ppm similarly to the content in the silica gel prepared in Example 2. The reaction results are described in Table 5.

Example 20

The reaction was carried out in the same manner as in Example 19, except that the concentration of Ag supported in the Ag/silica catalyst was changed to 10% and the acetone feed rate was changed to 1.70 g/h. The reaction results are described in Table 5.

Example 21

A silica gel was provided which had been prepared in accordance with the method described in Example 1 except that the amount of the aqueous aluminum nitrate solution in Example 1 was changed such that 200 ppm in terms of aluminum element would be supported. This silica gel as a dehydration catalyst weighing 10.0 g was combined with 7.87 g of a 10 wt % aqueous silver nitrate solution and 20 ml of ion exchange water. These materials were mixed together using a rotary evaporator at room temperature for 1 hour. Water was distilled away at a reduced pressure of 20 mmHg at 40 to 50° C. Thus, silver was supported on the silica gel. The obtained silica gel supporting silver and aluminum was subjected to a reduction treatment in which the temperature was increased stepwise from 100° C. to 300° C. in 5 hours under a stream of hydrogen. As a result, 10.5 g of a black 5% Ag-200 ppm Al/silica catalyst was obtained. The total content of alkali metals and alkaline earth metals in the Al-containing silica catalyst was 7 ppm. The 5% Ag-200 ppm Al/silica catalyst weighing 3.0 g was packed into a reactor to form a catalyst layer. The reaction was carried out in the same manner as in Example 19, except that the reaction temperature was changed from 300° C. to 260° C. The reaction results are described in Table 5.

TABLE 5

|  | Reaction temp. (° C.) | Reaction time (h) | Acetone feed rate (g/h) | Acetone conversion | Propylene selectivity (on the basis of acetone) |
|---|---|---|---|---|---|
| Ex. 17 | 300 | 27 | 0.3 | 94.3 | 90 |
| Comp. Ex. 10 | 300 | 27 | 0.3 | 58.0 | 2 |
| Ex. 18 | 300 | 45 | 0.3 | 92.9 | 89 |
| Ex. 19 | 300 | 23 | 0.3 | 97.7 | 94 |
| Ex. 20 | 300 | 44 | 1.7 | 99.0 | 95 |
| Ex. 21 | 260 | 52 | 0.3 | 99.9 | 96 |

Reaction results (mol %)

From the results of Examples 17 to 21 and Comparative Example 10 in Table 5, excellent acetone conversion and propylene selectivity on the basis of acetone are obtained by using the silica gel (A1) as a dehydration catalyst which contains alkali metals and alkaline earth metals at a total of 0 to 20 ppm as well as an aluminum compound at 10 to 1000 ppm in terms of aluminum element, in combination with the silver-containing inorganic substance as a hydrogenation catalyst.

Example 22

A 5% Ag-1% In/silica catalyst classified to sizes of 250 to 500 μm was obtained in the same manner as in Example 17. To form a catalyst layer, 6.0 g of the 5% Ag-1% In/silica catalyst obtained above and 1.0 g of the silica gel (A2) (a dehydration catalyst) used in Example 10 which supported 50 ppm of aluminum were mixed together sufficiently and packed into a SUS 316 reactor having an inner diameter of 1 cm.

The pressure was increased to 3.0 MPa with hydrogen. Under a stream of hydrogen at 22 ml/min, acetone was passed from the inlet side of the reactor at a rate of 0.30 g/h at 300° C.

Nitrogen was introduced at 50 ml/min in the middle between the reactor outlet and a back pressure valve through a high pressure nitrogen mass flow controller. Sampling was performed from a line located downstream from the back pressure valve, and the products were quantitatively determined by GC analysis. The reaction results are described in Table 6.

Comparative Example 11

A 5% Ag-1% In/silica catalyst was prepared and classified in the same manner as in Example 17. This catalyst weighing 5.0 g was mixed together sufficiently with 1 g of a catalyst in which heteropoly acid salt $H_{0.5}K_{2.5}PW_{12}O_{40}$ (potassium phosphotungstate in which the hydrogen atoms in the phosphotungstic acid were partially exchanged with potassium) was supported on silica with a weight ratio of 1:1. The mixture was packed into a reactor to form a catalyst layer. This catalyst in which $H_{0.5}K_{2.5}PW_{12}O_{40}$ was supported on silica with a weight ratio of 1:1 had been obtained by precisely reproducing the production described in Example 7 of Patent Literature 3 (WO 2010/106966). Thereafter, the reaction was carried out in the same manner as in Example 22. The reaction results are described in Table 6.

Example 23

A silica gel was provided which had been obtained by washing CARiACT (Q-10) with acetic acid as described in Example 6. Then, 7.87 g of a 10 wt % aqueous silver nitrate solution and 20 ml of ion exchange water were added to 10.0 g of the silica gel. These materials were mixed together using a rotary evaporator at room temperature for 1 hour. Water was distilled away at a reduced pressure of 20 mmHg at 40 to 50° C. Thus, silver was supported on the silica gel. This silica gel, which had been washed with acetic acid and caused to support silver as described above, was subjected to a reduction treatment in which the temperature was increased stepwise from 100° C. to 300° C. in 5 hours under a stream of hydrogen. As a result, 10.5 g of a black 5% Ag/silica gel catalyst washed with acetic acid was obtained. A 3.0 g portion of the catalyst was packed into a reactor to form a catalyst layer. The reaction was carried out in the same manner as in Example 22, except that the amount of hydrogen gas and the acetone feed rate were changed to 21.8 ml/min and 0.85 g/h, respectively. The reaction results are described in Table 6.

Comparative Example 12

The reaction was carried out in the same manner as in Example 22, except that the dehydration catalyst was changed to γ-alumina. The reaction results are described in Table 6.

TABLE 6

|  | Reaction temp. (° C.) | Reaction time (h) | Acetone feed rate (g/h) | Acetone conversion | Propylene selectivity (on the basis of acetone) |
|---|---|---|---|---|---|
| Ex. 22 | 300 | 130 | 0.3 | 98.0 | 95.3 |
| Comp. Ex. 11 | 300 | 130 | 0.3 | 94.1 | 94.0 |
| Ex. 23 | 300 | 122 | 0.85 | 97.2 | 95.2 |
| Comp. Ex. 12 | 300 | 110 | 0.3 | 67.1 | 74.2 |

Reaction results (mol %)

In Tables 5 and 6, the reaction time indicates the duration of time from the initiation of the reaction until the reaction results (acetone conversion, selectivity) were obtained.

From Table 6, it has been shown that propylene can be obtained with high selectivity by catalyzing the reaction with a mixture of the silver-supporting silica gel catalyst and the silica gel (A2) as a dehydration catalyst, or with a catalyst in which silver is supported on the silica gel (A2).

Comparative Examples 11 and 12, which involved a mixture of the silver-supporting silica gel catalyst and a known dehydration catalyst such as a heteropoly acid salt or γ-alumina, resulted in poor conversion and selectivity compared to the present invention.

INDUSTRIAL APPLICABILITY

The method of the present invention can produce an olefin with high efficiency by the intramolecular dehydration reaction of an alcohol even in the presence of a ketone without the occurrence of side reactions such as the Aldol condensation of the ketone. Further, the invention also provides a practical method in industry which can produce an olefin with high selectivity in a single reaction step by directly reacting a ketone and hydrogen. With this method, propylene can be produced directly from acetone that is by-produced in the phenol production by the cumene process.

The invention claimed is:

1. An olefin production method, comprising reacting an alcohol of Formula (I) below in a dehydration reaction using a chemically treated silica gel (A) as a dehydration catalyst to thereby produce an olefin represented by Formula (II) below, wherein the silica gel (A) contains 10 to 1000 ppm of aluminum and 0 to 350 ppm of a metal selected from the group consisting of an alkali metal, an alkaline earth metal, and combinations thereof:

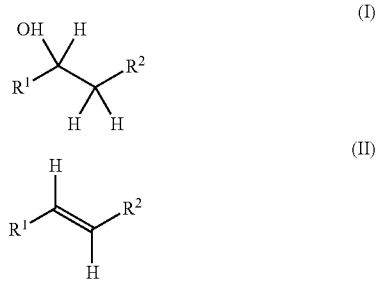

in Formulae (I) and (II), $R^1$ is a group selected from alkyl groups of 1 to 5 carbon atoms and aryl groups of 6 to 12 carbon atoms; and $R^2$ is an atom or a group selected from a hydrogen atom, alkyl groups of 1 to 5 carbon atoms and aryl groups of 6 to 12 carbon atoms.

2. The olefin production method according to claim 1, wherein the silica gel (A) is a silica gel (A1) which is obtained by bringing a silica gel (X) prepared from an alkyl orthosilicate into contact with a water-soluble aluminum compound and calcining the contact product and which contains 10 to 1000 ppm of aluminum and 0 to 20 ppm of a metal selected from the group consisting of an alkali metal, an alkaline earth metal, and combinations thereof.

3. The olefin production method according to claim 1, wherein the silica gel (A) is a silica gel (A2) which is obtained from a wet-process silica gel (Y) prepared from an alkali silicate and which contains 10 to 1000 ppm of aluminum and 1 to 350 ppm of a metal selected from the group consisting of an alkali metal, an alkaline earth metal, and combinations thereof.

4. The olefin production method according to claim 3, wherein the silica gel (A2) is a silica gel (A2-1) which is obtained by subjecting a wet-process silica gel (Y) prepared from an alkali silicate to a contact treatment with an acidic aqueous solution comprising a pH of 0.5 or greater and less than 7, and calcining the product.

5. The olefin production method according to claim 3, wherein the silica gel (A2) is a silica gel (A2-2) which is obtained by bringing a wet-process silica gel (Y) prepared from an alkali silicate into contact with a water-soluble aluminum compound, and calcining the contact product.

6. The olefin production method according to claim 3, wherein the silica gel (A2) is a silica gel (A2-3) which is obtained by subjecting a wet-process silica gel (Y) prepared from an alkali silicate to a contact treatment with an acidic aqueous solution comprising a pH of 0.5 or greater and less than 7, then bringing the product into contact with a water-soluble aluminum compound, and calcining the contact product.

7. The olefin production method according to claim 3, wherein the silica gel (A2) is a silica gel (A2-4) which is obtained by bringing a wet-process silica gel (Y) prepared from an alkali silicate into contact with a water-soluble aluminum compound, then subjecting the contact product to a contact treatment with an acidic aqueous solution comprising a pH of 0.5 or greater and less than 7, and calcining the product.

8. The olefin production method according to claim 1, wherein a ketone represented by Formula (III) below is present in an amount in terms of weight that is 0.01 to 10 times the amount of the alcohol represented by Formula (I):

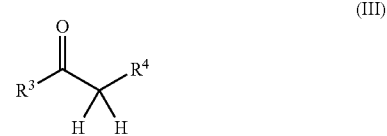

in Formula (III), $R^3$ is a group selected from alkyl groups of 1 to 5 carbon atoms and aryl groups of 6 to 12 carbon atoms; and $R^4$ is an atom or a group selected from a hydrogen atom, alkyl groups of 1 to 5 carbon atoms and aryl groups of 6 to 12 carbon atoms.

9. The olefin production method according to claim 8, wherein $R^3$ in Formula (III) is an identical group to $R^1$ in Formulae (I) and (II), and $R^4$ in Formula (III) is an identical atom or group to $R^2$ in Formulae (I) and (II).

10. An olefin production method, comprising producing an olefin represented by Formula (II) below from a ketone of Formula (III) below and hydrogen in a single reaction step in the presence of a chemically treated silica gel (A) which contains 10 to 1000 ppm of aluminum and 0 to 350 ppm of a metal selected from the group consisting of an alkali metal, an alkaline earth metal, and combinations thereof, and a silver-containing inorganic substance (B):

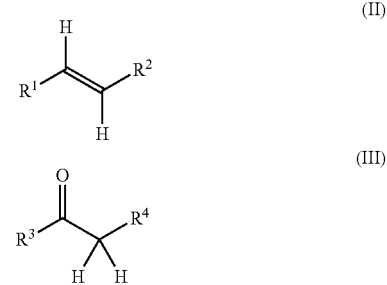

in Formula (II), $R^1$ is a group selected from alkyl groups of 1 to 5 carbon atoms and aryl groups of 6 to 12 carbon atoms; and $R^2$ is an atom or a group selected from a hydrogen atom, alkyl groups of 1 to 5 carbon atoms and aryl groups of 6 to 12 carbon atoms;

in Formula (III), $R^3$ is a group selected from alkyl groups of 1 to 5 carbon atoms and aryl groups of 6 to 12 carbon atoms; and $R^4$ is an atom or a group selected from a hydrogen atom, alkyl groups of 1 to 5 carbon atoms and aryl groups of 6 to 12 carbon atoms; and $R^3$ in Formula (III) and $R^1$ in Formula (II) are the identical groups, and $R^4$ in Formula (III) and $R^2$ in Formula (II) are the identical atoms or groups.

11. The olefin production method according to claim 10, wherein the silver-containing inorganic substance (B) contains at least one Group 13 (IIIA) element in the periodic table.

12. The olefin production method according to claim 8, wherein the ketone represented by Formula (III) is acetone, and the olefin represented by Formula (II) is propylene.

13. The olefin production method according to claim 10, wherein the reaction is carried out in the presence of a mixture of the silica gel (A) and the silver-containing inorganic substance (B).

14. The olefin production method according to claim 1, wherein the reaction is carried out at a temperature between 50 to 500° C.

15. The olefin production method according to claim 10, wherein the reaction is carried out at a temperature between 50 to 500° C.

* * * * *